United States Patent [19]

Hosokawa et al.

[11] 4,037,109
[45] July 19, 1977

[54] SAMPLE CELL

[75] Inventors: Yoshinori Hosokawa; Yoshihiro Wakiyama; Yazyuro Nomura, all of Kyoto, Japan

[73] Assignee: Horiba, Ltd., Kyoto, Japan

[21] Appl. No.: 634,739

[22] Filed: Nov. 24, 1975

[30] Foreign Application Priority Data

Nov. 26, 1974    Japan .......................... 49-144688[U]

[51] Int. Cl.² .......................................... G01N 23/10
[52] U.S. Cl. .................... 250/444; 250/272; 356/246
[58] Field of Search ............... 250/272, 273, 444; 356/246

[56] References Cited
U.S. PATENT DOCUMENTS

| | | | |
|---|---|---|---|
| 3,332,316 | 7/1967 | Saunders | 356/246 |
| 3,354,308 | 11/1967 | Engel et al. | 250/272 |
| 3,462,598 | 8/1969 | Burke et al. | 250/272 X |
| 3,498,724 | 3/1970 | Hayes et al. | 356/246 |

Primary Examiner—Archie R. Borchelt
Attorney, Agent, or Firm—Wenderoth, Lind & Ponack

[57] ABSTRACT

A sample cell useful in fluorescent X-ray analytical devices is provided herein, which cell is composed of an inner frame; an inner frame cover and a radiation-permeable sheet which houses the sample to be analyzed and an outer frame which covers the sample. The inner frame cover which is formed by bending a soft plastic film and the radiation-permeable sheet are such that they may be discarded after each analysis whereas the inner frame and the outer frame are used for reinforcement and sealing up of the sample and are never contaminated with the sample to be analyzed. Since the inner frame cover and the X-ray permeable sheet are the only members of the sample cell which contact the sample to be analyzed, these portions have been made from inexpensive disposable materials so that they can be discarded after each X-ray analysis, thereby eliminating the need to wash the sample cell after each analysis. Since the inner frame and the outer frame are not in contact with the sample to be analyzed, these portions may be used repeatedly in conjunction with each new disposable inner frame cover and radiation-permeable sheet. According to the present invention, the troublesome and laborious cleaning operation necessary in conventional sample cells is eliminated and further, contamination of the hands or clothes by the sample to be analyzed is prevented.

4 Claims, 4 Drawing Figures

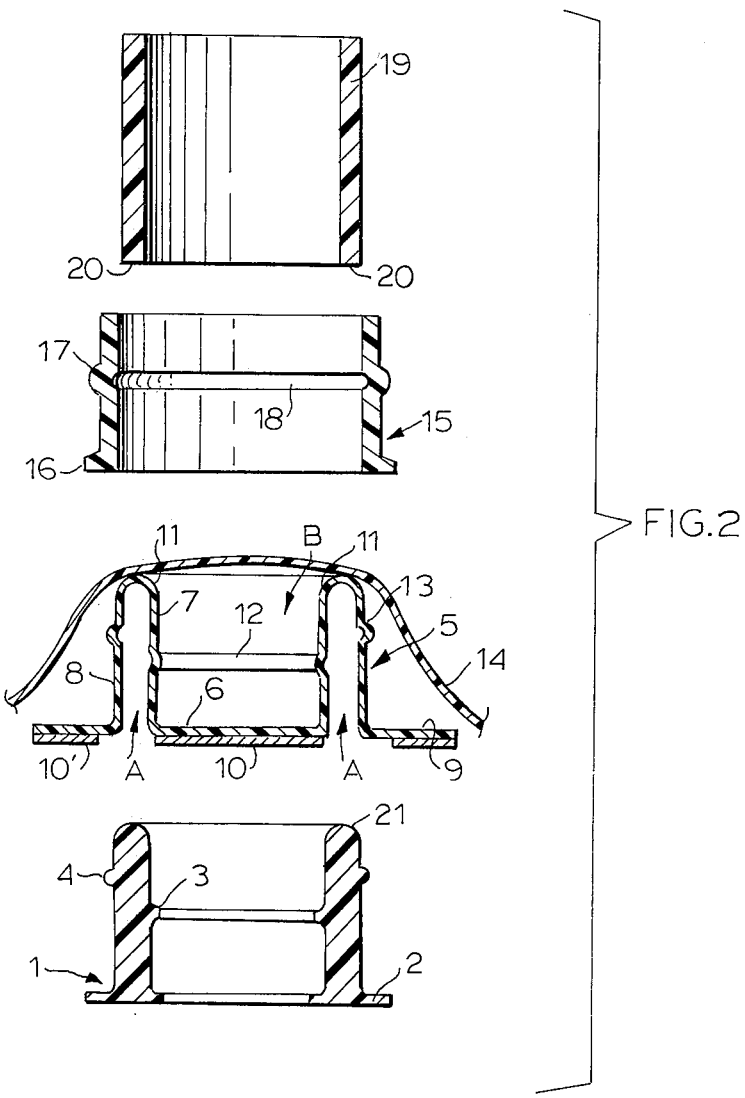
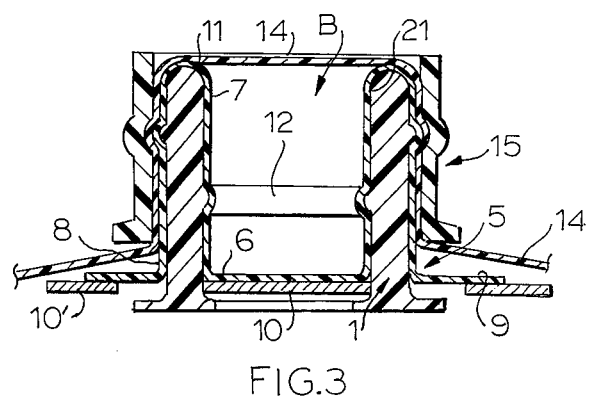

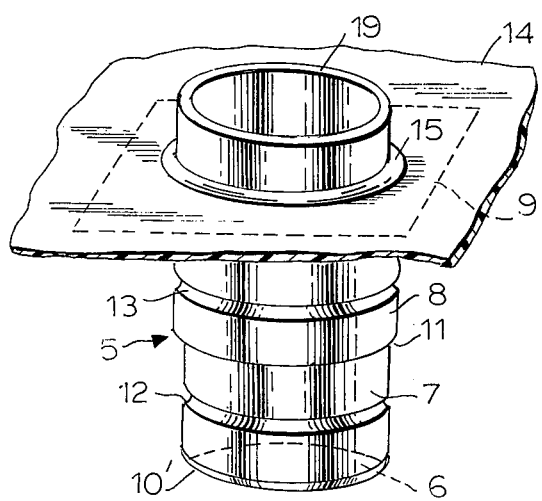
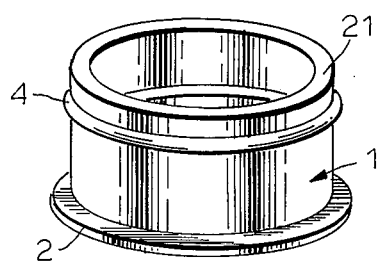
FIG.4

SAMPLE CELL

BACKGROUND OF THE INVENTION

This invention relates to a sample cell to be used in, e.g. flourescent X-ray analytical devices.

DESCRIPTION OF THE PRIOR ART

With regard to such kind of sample cell, it has been used repeatedly by performing cleaning every time when a prescribed analytical operation has been finished as customary practice. Although this is due to such a reason that sample cell is comparatively expensive, such cleaning operation was troublesome since it requires considerable labor and also it contaminated hand or clothes, etc. Further, there was such defects that its construction being complex and higher cost, and also its assembling and disassembling require much labor.

SUMMARY OF THE INVENTION

This invention resolves above-mentioned defects in customary device by making its one part a discarding member, and its object is to provide a device of which handling becomes extremely simple and low cost in spite of discarding type, and also it has superior function as sample cell.

BRIEF DESCRIPTION OF THE DRAWINGS

Drawings show one practical embodiment of this invention, and:

FIG. 2 is a longitudinal section at assembled state.
FIG. 3 is a longitudinal section at assembled state.
FIG. 4 is a perspective view showing a state under disassembling of device.

DETAILED DESCRIPTION OF A PREFERRED EMBODIMENT

Figure 1:
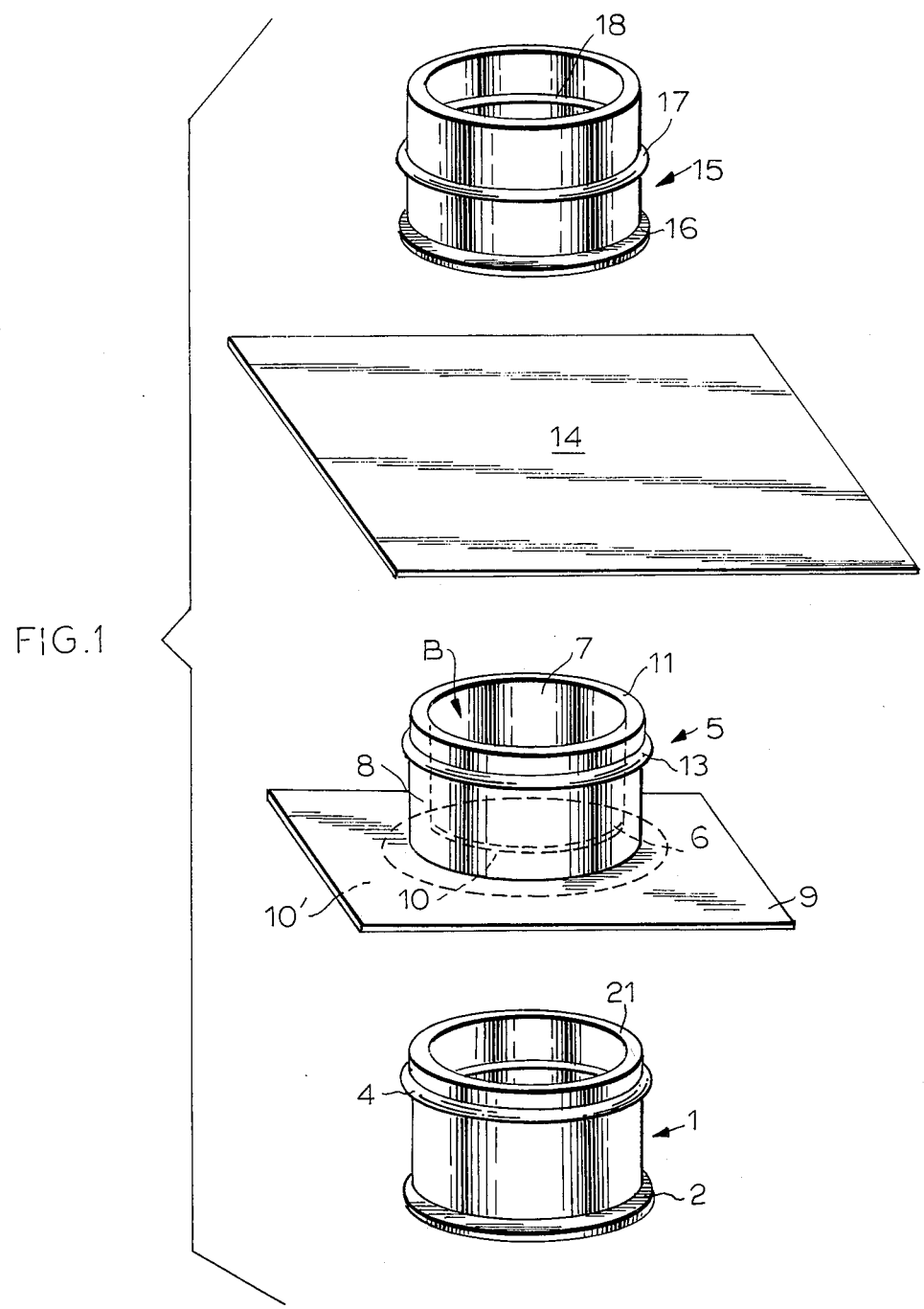
FIG. 1 is a perspective view at disassembled state.

One practical embodiment of this invention will be explained referring to the drawings as follows.

1 is an inner frame made of plastic such as polyethylene (it may be made of metal, etc.), and formed as substantially cylindrical shape, and annular projections 2, 3, 4 are provided properly at its lower part and side part. 5 is an inner frame cover formed by bending soft plastic film, and it has circular bottom part 6, annular uprising part 7 surrounding this circular bottom part 6, turndown part 8 connected with upper end of uprising part 7 and flange part 9. 10,10' are mounting paper to reinforce inner frame cover 5 and stuck onto back face of circular bottom part 6 and flange part 9. And, space A formed by said uprising part 7 and turndown part 8 is made a largeness in which said inner frame 1 being fitter entirely, and connection point 11 between uprising part 7 and turndown part 8 is formed so as to become smooth circular arc shape. And 12, 13 is annular project 10, provided on uprising part 7 and turndown part 8, respectively, and the former forms a standard line when sample being poured. 14 is a radiation-premeable sheet made of, e.g. polyester phthalate, and 15 is outer frame made of plastic such as polyethylene (it may be made of metal, etc.) formed as substantially circular shape, and annular projections 16, 17 and cavity 18 are provided properly at its lower part and side part.

In order to assemble this sample cell, as shown in FIG. 3, first inner frame 1 is fitted into said space A of inner frame cover 5 so that uprising part 7 and turndown part 8 of inner frame cover 5 covers inner frame 1 as a whole, then liquid sample is poured into space B formed by bottom part 6 and uprising part 7 of inner frame cover 5 up to the neighborhood of said standard line 12, and then radiation-permeable sheets 14 is covered from upper side, and further said outer frame 15 is fitted from upper side. When this outer frame 15 is fitted, radiation-permeable sheet 14 is pulled by outer frame 15 and spread without producing any crease, and also it contacts closely with said circular arc shaped connection point 11 so as to prevent sample from leaking out of sample cell. And, at this state, sample cell is charged into fluorescent X-ray analyzing device at upside-down state, and primary X-ray is irradiated from lower side passing through radiation-permeable sheet 14, and fluorescent X-ray as analytic element in sample is ecited so as to measure its energy and strength. After measurement has been finished, sample cell is removed from said fluorescent X-ray analyzing device, and e.g. a cylindrical disassembling implement 19 as shown in FIG. 2 and FIG. 4 is inserted inside the outer frame 15, and lower end face 20 of this implement 19 is applied to upper end face 21 of inner frame and said circular arc shaped connection point 11 covering this upper end face 21, and outer frame 15, radiation-permeable sheet 14 and inner frame cover 5 are removed from inner frame 1 as shown in FIG. 4 by pulling flange part 9 of inner frame cover 5 upwards and turning over said turndown part 8. At this time, said liquid sample lies within the space surrounded by bottom part 6 of inner frame cover 5, uprising part 7 and turndown part 8, and there is no fear of leaking to outside. Then, inner frame cover 5, liquid sample and radiation-permeable sheet 14 may be discarded or preserved after outer frame 15 and disassembling implement 19 were removed.

This invention is constituted as described above, and it has effects as follows.

1. By making only inner frame cover and radiation-permeable sheet a discarding member, troublesome and laborious cleaning operation as in customary device become perfectly unnecessary, besides contamination of hand or clothes is prevented.

Moreover, discarding member is only inner frame cover and radiation-permeable sheet to which sample is stuck, and these members can be manufactured at low price, while inner frame and outer frame which is comparatively high price can be used repeatedly, according whole cost is low enough in spite of discarding type, and analytic cost can be reduced remarkably as a whole.

2. It is easy to form connection point between uprising part and turnddown part as smooth circular arc shape without any creases since inner frame cover is formed by bending a plastic film.

And, radiation-permeable sheet can be extended at definite tension without producing any creases, since said connection part has no creases and outer frame is fitted from upper side of radiation-permeable sheets, as the result reproductive property is improved.

3. Complete sealing of sample becomes possible since said radiation-permeable sheets can be contacted closely with connection point between uprising part and turndown part, and poured sample can be preserved without fear of changing in quality or leaking to outside.

In the sample cell according to this invention, manufacturing cost is low price and also its assembling is easy by its construction and disassembling is easy by the use of, e.g. a cylindrical shaped disassembling implement.

What is claimed is:

1. A sample cell comprising a disposable inner frame cover (5) formed by bending a plastic film, said cover having a bottom part (6), an uprising part (7), a connection part (11), a turndown part (8) and a flange part (9); said uprising part (7), connection part (11) and turndown part (8) of said inner frame cover being covered onto a cylindrical shaped inner frame (1); a disposable plastic radiation-permeable sheet (14) covering the upper side of said inner frame cover and a cylindrical shaped outer frame (15) fitted onto the upper side of said inner frame cover over said radiation sheet (14); said sample cell being characterized in that a sample to be analyzed by X-ray analysis only contacts the disposable inner frame cover (5) and the disposable radiation-permeable sheet (14) so that such disposable parts can be discarded after each analysis and replaced by clean disposable parts, thereby avoiding the necessity of washing the sample cell.

2. A sample cell as defined by claim 1, said connection part (11) being formed in the shape of a smooth circular arc.

3. A sample cell as defined by claim 1, wherein a reinforcing mounting paper (10, 10') is stuck onto said bottom part (6) and flange part 9, respectively.

4. A sample cell as defined by claim 5, wherein annular convex or concave parts (3), (12); (4), (13), (18) to be fitted mutually are provided on the side faces of said inner frame (1), inner frame cover (5) and outer frame (15), respectively.

* * * * *